United States Patent
Ingo et al.

(10) Patent No.: US 8,357,338 B2
(45) Date of Patent: Jan. 22, 2013

(54) APPARATUS FOR GENERATING A MULTI-COMPONENT COMPOUND

(75) Inventors: Wagner Ingo, Woerthsee (DE); Helmut Pauser, Diessen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 1768 days.

(21) Appl. No.: 10/591,257

(22) PCT Filed: Mar. 1, 2005

(86) PCT No.: PCT/EP2005/002151
§ 371 (c)(1),
(2), (4) Date: Aug. 31, 2006

(87) PCT Pub. No.: WO2005/084579
PCT Pub. Date: Sep. 15, 2005

(65) Prior Publication Data
US 2007/0175918 A1    Aug. 2, 2007

(30) Foreign Application Priority Data
Mar. 1, 2004   (EP) ..................................... 04004668

(51) Int. Cl.
G01F 11/00   (2006.01)
B65D 88/54   (2006.01)
B01L 3/00    (2006.01)
B01L 3/02    (2006.01)

(52) U.S. Cl. ........... 422/521; 222/63; 222/333; 422/500
(58) Field of Classification Search .................. 422/100; 433/89; 222/1, 52, 63
See application file for complete search history.

(56) References Cited

U.S. PATENT DOCUMENTS

| | | | |
|---|---|---|---|
| 5,286,105 A | 2/1994 | Herold et al. | 366/177 |
| 5,605,252 A * | 2/1997 | Owen et al. | 222/1 |
| 5,630,527 A | 5/1997 | Beebe et al. | 222/1 |
| 5,788,927 A * | 8/1998 | Farrell et al. | 422/63 |
| 5,853,774 A | 12/1998 | Dreve | 425/87 |
| 6,168,052 B1 | 1/2001 | Keller | 222/333 |
| 6,315,164 B1 | 11/2001 | Mühlbauer et al. | 222/63 |
| 6,371,336 B1 | 4/2002 | Keller | 222/333 |
| 6,500,001 B2 | 12/2002 | Hörth et al. | 433/89 |
| 6,575,331 B1 | 6/2003 | Peeler et al. | 222/1 |
| 6,932,237 B2 | 8/2005 | Heymann et al. | 222/1 |
| 2003/0022128 A1 | 1/2003 | Heymann et al. | 433/89 |

FOREIGN PATENT DOCUMENTS

| | | |
|---|---|---|
| EP | 0 492 413 | 7/1992 |
| EP | 0 956 908 | 11/1999 |
| EP | 1 010 401 | 6/2000 |
| EP | 1 101 538 | 5/2001 |
| EP | 1 279 379 | 1/2003 |

* cited by examiner

*Primary Examiner* — Dean Kwak
(74) *Attorney, Agent, or Firm* — Carlos M. Téllez

(57) ABSTRACT

The invention relates to an apparatus for generating a multi-component compound, in particular for dental purposes, comprising: —At least two cartridges (3), each cartridge (3) adapted for containing a component (4) of the multi-component compound and having a plunger (2) adapted for pressing out its component (4) from the cartridge (3); and—a driving device for said plungers (2) in which the driving speed is adjustable, wherein the driving device comprises a stepping motor (1), and a detector associated with the stepping motor for detecting at least one of a) the steps of the stepping motor and b) The load on the stepping motor. At low revolutions per minute, the stepping motor (1) offers higher torque as compared with the known DC motors, whereas it also offers high revolutions per minute, although with comparatively low torque, sufficient for rapid advance and retraction of the plungers (2).

13 Claims, 1 Drawing Sheet

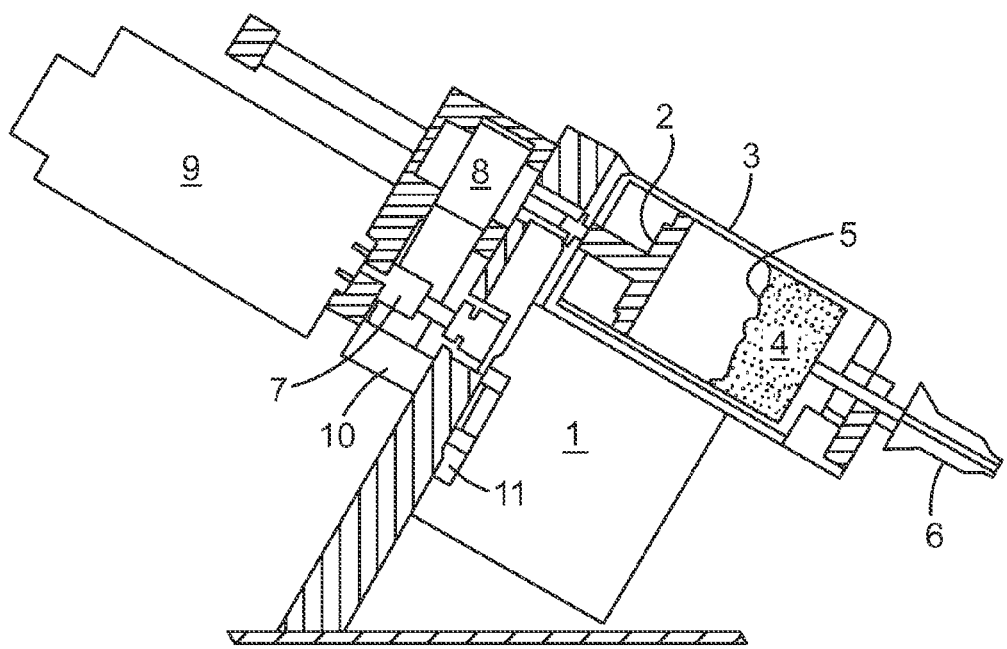

APPARATUS FOR GENERATING A MULTI-COMPONENT COMPOUND

BACKGROUND OF THE INVENTION

1. Technical Field

The present invention relates to a apparatus and to a method, for generating a multi-component compound, in particular for dental purposes.

2. Description of the Related Art

In general, known apparatuses for generating a multi-component compound for dental purposes operate by pressing its typically high viscous components out from exchangeable cartridges. These cartridges are arranged side-by-side, and they open into a static or dynamic mixer. An electric drive acts on plungers associated with the cartridges to advance them jointly for pressing out the components. In some apparatuses, the plungers are driven by motors that are not regulated or controlled at all. This leads to varying revolutions per minute and therefore to varying plunger velocities, which affects the mixing quality and application time. Within these apparatuses it is not possible to adapt the plunger velocity and mixer speed to the various paste characteristics with little expenditure.

There exist also other known apparatuses and methods, wherein the advance speed of the plungers is adjustable. It is generally desired that the plungers be advanced for positioning rapidly. When the plungers make contact with the components, the resistance and therefore the load for the drive increases. The advance speed should then be regulated to a lower constant value in order to ensure that the components are pressed out at a uniform speed.

Furthermore, it has been found that in many cases it is not sufficient to regulate the advance speed to a constant value. Instead it is also necessary to select the suitable advance speed due to different types of components, which have very different properties, e.g. viscosities, or which require particular speeds due to processing factors. Depending on the properties of the components, there is an optimum advance and a good and reproducible result of the work.

EP 1 101 538 A2 and U.S. Pat No. 6,371,336 B1 each discloses an electrically operated dispensing appliance. This known appliance comprises a gear motor which is connected to the main shaft by a first gear and a first shifting sleeve in order to operate the advance and the relieving stroke under high loads. For the operation at smaller loads, i.e. fast retraction and fast forward feed, it is connected to the main shaft by a second gear, a driving shaft, and a second shifting sleeve. An electromagnet is connected to said two shifting sleeves in such a manner that one or the other shifting sleeve is selectively connectable to the main shaft.

EP 0 956 908 A1 and U.S. Pat. No. 6,168,052 B1 each discloses an electrically driven dispensing appliance. This known appliance comprises an electric drive that acts via drive screws on thrust plates for dispensing material from cartridges. The different forces acting upon the two drive screws are supported by rolling friction on low friction bearings so that no tilting forces on the slide are generated. The electric drive comprises a first gear motor for a drive under high load during advance and relief, and a second motor for the drive under lower load during the retracting and fast advance motions.

EP 0 492 413 A1 and U.S. Pat. No. 5,286,105 each discloses an apparatus for mixing and applying two-component materials. This known apparatus comprises two pistons which can be displaced and driven forward together by an electric motor via a magnetic coupling in the cartridges. The pistons can be drawn back manually. and inserted again via a manual wheel when the motor is switched off and the magnetic coupling moved out. In this application the motor drive is only designed for a slow advance of the pistons, wherein the changing of the cartridges is due to the manual extension and retraction of the pistons.

EP 1 010 401 A1 and U.S. Pat. No. 6,315,164 B1 each discloses a method and apparatus for generating a multi-component compound, in particular for dental purposes, by pressing its components out from exchangeable cartridges into a mixer. In this known apparatus, the advance speed is constantly kept at a predetermined value, to ensure that the mixing quality is not adversely affected by the advance speed differing depending on viscosity and friction ratios. This is preferably achieved by means of a unit which is assigned to the drive motor. This unit can also be used for driving the motor, depending on the load, either at a low speed assigned to the normal advance, or at a higher speed assigned to the return movement.

EP 1 279 379 A1 and US 2003/0 022 128 A1 each discloses an apparatus for generating a multi-component compound, in particular for dental purposes, by pressing out and mixing its components from cartridges which open into a mixer. In this known apparatus the advance speed of the electric motor is regulated by the pressing-out behavior of the components, which pressing-out behavior can be determined by sensors. Preferably, the electric motor is a DC motor.

In view of the above, to ensure a desired driving, i.e. advancing and returning speed of the plungers, DC motors are used in general. The torque characteristic of DC motors or shaded pole motors is the opposite of what is needed for the application, because they offer low torque at the low speed drive modus, whereas high torque is needed for pressing out the components. Furthermore, at very low speeds, of about 1 to 10 revolutions per minute, the operation of a conventional DC motor actually breaks down.

These drawbacks are often countered by complex gearboxes, manual interactions of users, a plurality of motors, or a plurality of driving units assigned to the drive motor and linked with additional sensors.

SUMMARY OF THE INVENTION

The present invention provides an improved motor concept for driving the plungers and shows the features of the claims.

The present invention provides the advantage that the motor concept provides both, higher torque at low speed for pressing out the components, and high speed for rapid positioning the plungers, by using only one motor, but without using a clutch and without the need of complex gearboxes and the need of changing gears.

The present invention provides the further advantage that the motor concept automatically adjusts the driving speed to a suitable value for the corresponding components.

The present invention relates to an apparatus for generating a multi-component compound, in particular for dental purposes, comprising:

at least two cartridges, each cartridge containing a component of the multi-component compound and having a plunger adapted for pressing out its component from the cartridge; and a driving device for said plungers in which the driving speed is adjustable, wherein the driving device comprises a stepping motor.

The present invention also relates to an apparatus for generating a multi-component compound, in particular for dental purposes, comprising:

at least two cartridges, each cartridge adapted for containing a component of the multi-component compound and having a plunger adapted for pressing out its component from the cartridge; and a driving device for said plungers in which the driving speed is adjustable, wherein the driving device comprises a stepping motor, and a detector associated with the stepping motor for detecting at least one of a) the steps of the stepping motor and b) the load on the stepping motor.

The present invention also relates to a method for generating a multi-component compound, in particular for dental purposes, by pressing out and mixing its components from at least two cartridges by driving plungers inside the cartridges by means of a driving device in which the driving speed is adjustable, wherein a stepping motor for driving the plungers is provided.

With this apparatus and method, the multi-component compound is generated by dispensing each component with a plunger of its cartridge into a mixer, wherein at least two components are mixed to generate the desired compound.

The stepping motor according to the present invention is surprisingly found to have the ideal torque and control characteristics for such an application. At low revolutions per minute, the stepping motor offers higher torque as compared with the known DC motors, whereas it also offers high revolutions per minute, although with comparatively low torque, sufficient for rapid advance and retraction of the plungers. This high torque at low revolutions per minute provides a high plunger pressure which is advantageous and necessary as the components, which are typically high viscous pasty materials, can only be dispensed from the cartridge with high application forces. On the other side, the comparatively low torque at high revolutions per minute provided by the stepping motor, is suitable since the high speed of the plungers is only used to position the plungers in a short time; therefore only low driving and motion forces are needed. Furthermore, a stepping motor according to the invention even provides a high torque for very low revolutions per minute (of about 1 to 10) since the stepping motor is able to drive very small individual steps.

These advantageous characteristics of the stepping motor make is possible to use only one motor for the two requirements of low speed with high torque and of high speed, even with low torque, without using complex gear boxes and without changing any gears.

Said driving device may be any kind of means for driving the plungers.

Further preferred features and embodiments of the invention are described in the claims.

A further advantage of stepping motors is the precise adjustment of the number of rotation steps and the driving speed by means of a driving unit. The driving device according to the present invention may comprise a driving unit for driving, controlling and monitoring the steps of the stepping motor. In addition to the precise adjustment of the rotation of the stepping motor, the steps can be easily monitored by the driving unit which corresponds in this application under certain circumstances to a monitoring of the plunger position. This monitoring of the plunger position may be achieved by, e.g., simply monitoring or counting the driving steps of the stepping motor. The driving device with the driving unit may therefore monitor and detect, whether the plunger is in an empty position, which relates to a plunger position at the front end of the cartridge when the cartridge is empty, or whether the plunger starts from a replacement position, which relates to a plunger position at the rear end so that a replacement of cartridges is possible, and advances to an initial position, in which the plunger gets into contact with the component level of a newly inserted cartridge.

Said driving unit may be any kind of means for driving, controlling and monitoring the steps of the stepping motor.

A further advantage of a driving device comprising a stepping motor is the capability to detect the status of the load of the stepping motor easily by a driving device which comprises a detector for detecting the load of the stepping motor. There are different methods to detect whether the status of load of the motor is in a load state or in an unload state. According to a first method, when the plunger advances and arrives at the component level, the status of load of the motor raises which results in an increase of the electric current and therefore in a change of the current response of the coils. A stepping motor additionally has the advantage that the detector may detect the status of load, according to a second method, by detecting and monitoring a change in the step frequency, or, according to a third method, by monitoring and detecting a loss of driving steps.

Said detector may be any kind of means for detecting the status of load of the stepping motor.

It is possible that the driving device is adapted to drive the stepping motor at a constant predetermined speed. This may easily be achieved by monitoring the driving steps of the stepping motor.

It is possible that the driving device is adapted to drive the stepping motor at different predetermined constant speeds which may be necessary for different applications, different components with different viscosities or for different generated compounds by different dispensing speeds.

Due to the fact that the stepping motor provides the ideal torque characteristic with the ideal control characteristic, the driving device can be designed very compact and simple without using complex and complicated gearboxes. For instance, it is possible that the output shaft of the stepping motor is connected directly, or via a belt, or via a simple construction with wheels and/or gear wheels and/or toothed chains and/or toothed belts, to the plunger or to each device for moving the plunger. Therefore the driving device with the stepping motor and the mechanical connection to the plunger is smaller, quieter, lighter in weight, and more reliable than the driving devices in the prior art.

Said moving device may be any kind of means for moving at least one of the plungers.

Since the stepping motor can be controlled very precisely in speed, the change of speed can be realized very fast so that a change of the plunger velocity is apparent in a very short time. This results in a shorter process time and in an improved handling for the end user, for instance when replacing cartridges. Furthermore, the very fast response of the stepping motor prevents an uncontrolled compound dispensing when the plunger arrives at the level of the components after a new cartridge has been inserted and the plunger moves into the initial position.

The stepping motor can also be used for driving a dynamic mixer which may be connected to the output shaft of the stepping motor. Due to the use of only one motor the speed of the mixer is automatically adjusted to the speed of the advancing plunger. However, it is possible to provide a separate motor for driving the mixer which opens the possibility to control the mixer speed as needed independently from the plunger speed.

The apparatus according to the present invention can therefore be built small and effective with an enhanced mixing quality and an optimized application time. The handling for the user is improved since the replacement of cartridges can be done in shorter time. Components with different physical characteristics, like different viscosities, can be used without disadvantages for generating and mixing. Due to the short positioning procedure it is also possible to adjust the speed of the plungers from fast to low automatically after a predetermined time period, preferably of 3 to 5 seconds, without using a detection signal in general. This time period may be calculated from the fast advance speed and the axial length of the cartridges' interior, so that during that time the correct position of the plungers at the component level is reached in every case, even in case of a nearly empty cartridge, i.e. a very low component level.

It is possible, that the method comprises the steps that:
the plungers are advanced with high speed into an initial position in which they get in contact with the components;
the data of this initial position is detected;
the plungers are retracted with high speed for a predetermined relief distance;
the plungers are advanced with high speed either for a predetermined bias distance greater than the relief distance, or until the components begin flowing out of the cartridges or into the mixer;
the plungers are driven with low speed for pressing out the components from the cartridges.

The data of this initial position may be detected to calculate the relief distance and/or the bias distance.

After having dispensed the desired amount of compound, the plungers may be retracted with high speed for relief of the components.

It is possible, that the method comprises the steps that:
during driving the plungers with low speed for pressing out the components from the cartridges, the pressing force or load of the stepping motor is monitored and compared with a predetermined upper limit;
if the upper limit is reached or exceeded, the stepping motor is stopped or adjusted to a lower speed.

The monitoring of the load may achieved by monitoring the electric current fed to the stepping motor or the driving steps or the step frequency, as described above.

The upper limit may depend on the different properties, e.g. viscosity, of the components, and may be entered into the apparatus either manually or automatically.

BRIEF DESCRIPTION OF THE DRAWINGS

Preferred embodiments of the invention are described in more detail below with reference to the attached drawings, which are by way of example only.

FIG. 1 is a partially cutaway side view of an apparatus for generating a multi-component compound according to a preferred embodiment of the present invention.

DETAILED DESCRIPTION OF PREFERRED EMBODIMENTS

FIG. 1 is a schematic representation of an apparatus for generating a two-component compound.

In the side view of FIG. 1, the cross section of only one cartridge 3 of two side-by-side cartridges, can be seen. An output shaft 10 of a stepping motor 1 is connected via a belt to a device 8 for moving a plunger 2. The detector is shown schematically at 11. This moving device 8 may comprise any kind of axle and/or drive screws and/or shaft, to move the plunger 3. As indicated by component level 5, the cartridge 3 is only half filled with one component 4 of the two components to be mixed.

The plunger 2 is in the depicted situation in FIG. 1 not in contact with the component 4. If a first cartridge shall be replaced with a second cartridge, the plunger 2 must be in a replacement position, i.e. at the rear end of the cartridge 3, so that the first cartridge may be removed from the apparatus and the second cartridge may be inserted into the apparatus. After the second cartridge 3 has been inserted, the plunger 2 is driven or advanced with high speed from the replacement position through an intermediate position, as indicated in FIG. 1, to an initial position in which the plunger 2 is in contact with the component level 5.

After driving the plunger 2 into contact with the component level 5, the apparatus is ready for generating and dispensing the two-component compound. Due to the high viscosity of the components, the plunger 2 can only be driven at a lower speed but with higher torque and thus dispenses the component 4 out from the cartridge 3 into the mixer 6. The component of the second cartridge (not shown in this kind of cross-sectional view), is dispensed as well in a like manner to the mixer 6, and the mixer 6 mixes the two components from the two cartridges 3 and generates the two-component compound.

In the embodiment of the apparatus shown in FIG. 1, the mixer 6 is a dynamic mixer and driven by a separate motor 9 and an output shaft 7.

However, it is also possible, that the dynamic mixer 6 is driven by the same stepping motor 1, or that the mixer is a static mixer in which case there is no need for motor 9.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. An apparatus for generating a multi-component compound, in particular for dental purposes, comprising:
   at least two cartridges (3), each cartridge (3) adapted for containing a component (4) of the multi-component compound and having a plunger (2) adapted for pressing out its component (4) from the cartridge (3); and
   a driving device for said plungers (2) in which the driving speed is adjustable,
   wherein the driving device comprises a stepping motor (1), and a detector associated with the stepping motor for detecting at least one of
   a) the steps of the stepping motor and
   b) the load on the stepping motor.

2. An apparatus according to claim 1, wherein the detector detects the status of load by the step frequency of the stepping motor (1).

3. An apparatus according to claim 1, wherein the detector detects the increase of load by a change or loss of driving steps of the stepping motor (1).

4. An apparatus according to claim 1, wherein the driving device is adapted to drive the stepping motor (1) at a predetermined constant speed.

5. An apparatus according to claim 1, wherein the driving device is adapted to drive the stepping motor (1) at different predetermined essentially constant speeds for one or different components and compounds.

6. An apparatus according to claim 1, wherein a predetermined speed of the stepping motor (1) is essentially constant when the stepping motor (1) is under load and at a higher speed in the absence of load.

7. An apparatus according to claim 1, wherein the stepping motor (1) is able to drive the plungers (2) at low speed with high torque and at higher speeds.

8. An apparatus according to claim 1, wherein an output shaft (7) of the stepping motor (1) is connected directly, or via a belt, or via wheels and/or gear wheels and/or toothed chains and/or toothed belts, to each device (8) for moving the plunger (2).

9. An apparatus according to claim 1, wherein the driving device is adapted to monitor the position of the plungers (2).

10. An apparatus according to claim 1, wherein the driving device is adapted to monitor the position of the plungers (2) by monitoring the driving steps of the stepping motor (1).

11. An apparatus according to claim 1, wherein the driving device is adapted to detect and monitor an empty position of a plunger (2) when said respective cartridge (3) is empty.

12. An apparatus according to claim 1, wherein the driving device is adapted to detect when the plungers (2) contact the components (4) after inserting the cartridges (3).

13. A system for generating a multi-component compound, in particular for dental purposes, with an apparatus according to claim 1 further comprising a mixer (6).

* * * * *

UNITED STATES PATENT AND TRADEMARK OFFICE
CERTIFICATE OF CORRECTION

PATENT NO. : 8,357,338 B2  
APPLICATION NO. : 10/591257  
DATED : January 22, 2013  
INVENTOR(S) : Ingo Wagner Page 1 of 1

It is certified that error appears in the above-identified patent and that said Letters Patent is hereby corrected as shown below:

Title Page  
Item (54) and  
Column 1, line 1  
(Title)

After "APPARATUS," insert -- AND METHOD --, therefor.

In the Drawing Sheet 1 of 1  
Lines 1-7 (Approx.)

Below " 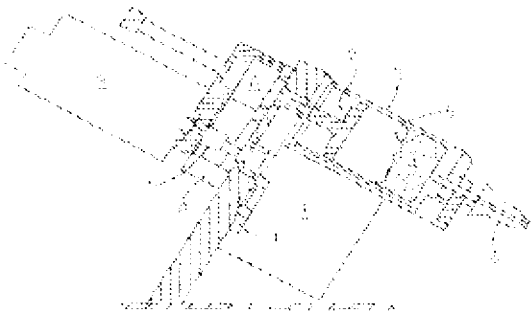 " insert -- FIG. 1 --.

In the Specifications  
Column 1  
Line 67

Delete "manually." and insert -- manually --, therefor.

Signed and Sealed this  
Eleventh Day of June, 2013

Teresa Stanek Rea  
*Acting Director of the United States Patent and Trademark Office*